US011900728B2

(12) United States Patent
Su et al.

(10) Patent No.: US 11,900,728 B2
(45) Date of Patent: *Feb. 13, 2024

(54) IRIS CAPTURE APPARATUS, IRIS CAPTURE METHOD, AND STORAGE MEDIUM

(71) Applicant: NEC Corporation, Tokyo (JP)

(72) Inventors: Leiming Su, Tokyo (JP); Hiroaki Morita, Gunma (JP); Mamoru Inoue, Tokyo (JP)

(73) Assignee: NEC CORPORATION, Tokyo (JP)

( * ) Notice: Subject to any disclaimer, the term of this patent is extended or adjusted under 35 U.S.C. 154(b) by 65 days.

This patent is subject to a terminal disclaimer.

(21) Appl. No.: 17/683,526

(22) Filed: Mar. 1, 2022

(65) Prior Publication Data
US 2022/0189203 A1 Jun. 16, 2022

Related U.S. Application Data

(63) Continuation of application No. 17/375,309, filed on Jul. 14, 2021, which is a continuation of application
(Continued)

(30) Foreign Application Priority Data
Aug. 24, 2016 (JP) ................... 2016-163434

(51) Int. Cl.
G06K 9/00 (2022.01)
G06V 40/19 (2022.01)
(Continued)

(52) U.S. Cl.
CPC ............ *G06V 40/19* (2022.01); *A61B 5/1171* (2016.02); *G06T 1/00* (2013.01); *G06T 7/00* (2013.01);
(Continued)

(58) Field of Classification Search
CPC ............ G06K 9/00; G06V 40/19; G03H 1/00; H04N 5/2258
(Continued)

(56) References Cited

U.S. PATENT DOCUMENTS 5,062,669 A * 11/1991 McManigal ............ E05B 81/10
292/DIG. 32
5,062,896 A 11/1991 Huang et al.
(Continued)

FOREIGN PATENT DOCUMENTS

EP 1 308 129 A2 5/2003
JP 09-196531 A 7/1997
(Continued)

OTHER PUBLICATIONS

JP Office Action for JP Application No. 2022-145813, dated Jul. 13, 2023 with English Translation.
(Continued)

*Primary Examiner* — Seyed H Azarian
(74) *Attorney, Agent, or Firm* — Sughrue Mion, PLLC

(57) ABSTRACT

The present invention provides a technology that acquires a high resolution iris image more quickly than before. An iris capture apparatus according to one example embodiment of the present invention includes a rotatable movable mirror; a control unit that controls rotation of the movable mirror; a capture unit that captures different regions of a face of a user via the movable mirror and outputs a group of images every time the control unit rotates the movable mirror by a predetermined angle; and an iris image acquisition unit that acquires an image of an iris of the user from the group of images.

10 Claims, 15 Drawing Sheets

Related U.S. Application Data

No. 16/689,783, filed on Nov. 20, 2019, now Pat. No. 11,093,741, which is a continuation of application No. 16/283,038, filed on Feb. 22, 2019, now Pat. No. 10,503,974, which is a continuation of application No. PCT/JP2017/030122, filed on Aug. 23, 2017.

(51) Int. Cl.

| | | |
|---|---|---|
| *G06T 1/00* | (2006.01) | |
| *G06T 7/00* | (2017.01) | |
| *A61B 5/1171* | (2016.01) | |
| *G06V 40/18* | (2022.01) | |
| *G06V 40/70* | (2022.01) | |

(52) U.S. Cl.
CPC .......... *G06V 40/193* (2022.01); *G06V 40/197* (2022.01); *G06T 2207/30201* (2013.01); *G06V 40/70* (2022.01)

(58) Field of Classification Search
USPC ........ 382/100, 103, 106, 115, 117, 118, 128, 382/155, 162, 168, 173, 181, 191, 199, 382/219, 224, 232, 254, 286–291, 176, 382/305, 296, 321; 348/46, 78, 208.5; 359/34, 554
See application file for complete search history.

(56) References Cited

U.S. PATENT DOCUMENTS

| | | | | |
|---|---|---|---|---|
| 5,294,991 | A * | 3/1994 | Oshima | H04N 23/6842 |
| | | | | 359/554 |
| 5,717,512 | A | 2/1998 | Chmielewski, Jr. et al. | |
| 7,068,820 | B2 * | 6/2006 | Nakaigawa | G06V 40/19 |
| | | | | 348/78 |
| 2007/0160265 | A1 * | 7/2007 | Wakiyama | G06V 40/19 |
| | | | | 382/117 |
| 2007/0216798 | A1 | 9/2007 | Northcott et al. | |
| 2012/0154536 | A1 * | 6/2012 | Stoker | H04N 23/45 |
| | | | | 348/208.99 |

FOREIGN PATENT DOCUMENTS

| | | | |
|---|---|---|---|
| JP | 10-137224 | A | 5/1998 |
| JP | 10-137225 | A | 5/1998 |
| JP | 10-340345 | A | 12/1998 |
| JP | 11-89820 | A | 4/1999 |
| JP | 2000-132681 | A | 5/2000 |
| JP | 2000-237169 | A | 9/2000 |
| JP | 2001-257929 | A | 9/2001 |
| JP | 2003-30659 | A | 1/2003 |
| JP | 2003-37766 | A | 2/2003 |
| JP | 2005-177166 | A | 7/2005 |
| JP | 2006-209213 | A | 8/2006 |
| JP | 2007-310429 | | 11/2007 |
| JP | 2009-080706 | A | 4/2009 |
| JP | 2010-108110 | | 5/2010 |
| JP | 2020-194599 | A | 12/2020 |
| WO | 2018/038158 | A1 | 3/2018 |

OTHER PUBLICATIONS

Japanese Office Action for JP Application No. 2020-147453 dated Feb. 8, 2022 with English Translation.
Japanese Office Action, dated Mar. 5, 2020, issued by the Japanese Patent Office in counterpart Japanese Patent Application No. 2018-535733.
International Search Report dated Oct. 31, 2017, in corresponding PCT International Application.
Extended European Search Report dated Aug. 19, 2019, in corresponding European Patent Office.
Office Action dated Jun. 2, 2020, issued by the Japanese Patent Office in counterpart Japanese Patent Application No. 2018-536733.
Japanese Office Action for JP Application No. 2020-147453 dated Sep. 24, 2021 with English Translations.

* cited by examiner

IRIS CAPTURE APPARATUS, IRIS CAPTURE METHOD, AND STORAGE MEDIUM

CROSS-REFERENCE TO RELATED APPLICATIONS

The present application is a continuation application of U.S. patent application Ser. No. 17/375,309 filed on Jul. 14, 2021, which is a continuation application of U.S. patent application Ser. No. 16/689,783 filed on Nov. 20, 2019, which issued as U.S. Pat. No. 11,093,741, which is a continuation application of U.S. patent application Ser. No. 16/283,038 filed on Feb. 22, 2019, which issued as U.S. Pat. No. 10,503,974, which is a National Stage Entry of international application PCT/JP2017/030122, filed on Aug. 23, 2017, which claims the benefit of priority from Japanese Patent Application 2016-163434 filed on Aug. 24, 2016, the disclosures of all of which are incorporated in their entirety by reference herein.

TECHNICAL FIELD

The present invention relates to an apparatus, a method, and a storage medium that capture an image of a human's iris.

BACKGROUND ART

In recent years, a technology of iris recognition that performs personal authentication using a human's iris has been put into practical use. Since a fine pattern of an iris is used for iris recognition, a high resolution iris image is required in order to realize iris recognition that satisfies sufficient accuracy. The high resolution image refers to, for example, an image of around 400 pixels in the vertical direction and around 400 pixels in the horizontal direction for an iris of one of the eyes.

A conceivable method of obtaining a high resolution iris image may be to cause a camera having a proximity lens to come close to the eye and capture it. However, it is inconvenient to move the user's eye close to the camera or move the camera close to the user's eye every time performing iris recognition.

To improve convenience at the user, it is desirable to capture a high resolution iris image at a position distant from the user. When an iris is captured at a position distant from the user, there is difficulty due to an uncertain position of the user or individual differences of the heights or the like among users. Further, since there is a limit in increase of the resolution of a camera, it is difficult to capture, in a short time at a high resolution, the entire range where the user's iris may be located. Thus, there is a demand for a technology of acquiring a high resolution iris image at a position distant from the user.

The art disclosed in Patent Literature 1 first acquires a plurality of images including a wide range by using a wide angle camera and then determines the position of a human's eye from a connected image formed of a plurality of images. The art then performs capturing with a telescope camera being focused on the position of the eye and acquires an image including an iris. With such a configuration, even when there is a positional shift of a user or there are individual differences among users, a high resolution iris image can be acquired.

The art disclosed in Patent Literature 2 first acquires an image including a person by using two human-position cameras and then detects the position in the vertical direction of an iris from the image. Next, the art adjusts the angle in the vertical direction of a mirror provided on a light path of an iris camera to the position of the iris and then captures a plurality of images by using the iris camera while rotating the mirror in the horizontal direction. The art then selects an image including the iris out of the plurality of images. With such a configuration, even when there is a positional shift of a user or there are individual differences among users, a high resolution iris image can be acquired.

CITATION LIST

Patent Literature

PTL 1: Japanese Patent Application Laid-Open No. H10-137224

PTL 2: Japanese Patent Application Laid-Open No. 2000-237169

SUMMARY OF INVENTION

However, both the arts disclosed in Patent Literatures 1 and 2 require at least two capture steps by using multiple types of cameras, which include a step of capturing a wide range image to determine the position of an iris and a step of capturing only the iris to acquire an iris image. Therefore, since both the arts disclosed in Patent Literatures 1 and 2 require long time for capturing and iris detection, which is inconvenient for the user and difficult to be applied to walk-through recognition in which iris recognition is performed on a moving user.

The present invention has been made in view of the problem described above and intends to provide a technology of acquiring a high resolution iris image more quickly than before.

A first example aspect of the present invention is an iris capture apparatus including: a rotatable movable mirror; a control unit that controls rotation of the movable mirror; a capture unit that captures different regions of a face of a user via the movable mirror and outputs a group of images every time the control unit rotates the movable mirror by a predetermined angle; and an iris image acquisition unit that acquires an image of an iris of the user from the group of images.

A second example aspect of the present invention is an iris capture method including steps of: rotating a rotatable movable mirror repeatedly by a predetermined angle; capturing different regions of a face of a user via the movable mirror and outputting a group of images every time rotating the movable mirror by a predetermined angle; and acquiring an image of an iris of the user from the group of images.

A third example aspect of the present invention is a storage medium that causes a computer to execute steps of rotating a rotatable movable mirror repeatedly by a predetermined angle; capturing different regions of a face of a user via the movable mirror and outputting a group of images every time rotating the movable mirror by a predetermined angle; and acquiring an image of an iris of the user from the group of images.

According to the present invention, capturing of different regions of a user's face is repeated with a movable mirror being rotated, and an image of a user's iris is acquired from a group of output images. Since the movable mirror can be rotated faster than a camera, it is possible to acquire an iris image more quickly. Further, since different regions of a user's face are captured with the movable mirror being rotated, it is possible to acquire a high resolution iris image without requiring multiple types of cameras.

DESCRIPTION OF EMBODIMENTS

While example embodiments of the present invention will be described below with reference to the drawings, the present invention is not limited to these present example embodiments. Note that, throughout the drawings illustrated below, components having the same function are labeled with the same reference, and the repeated description thereof may be omitted.

First Example Embodiment

Figure 1:
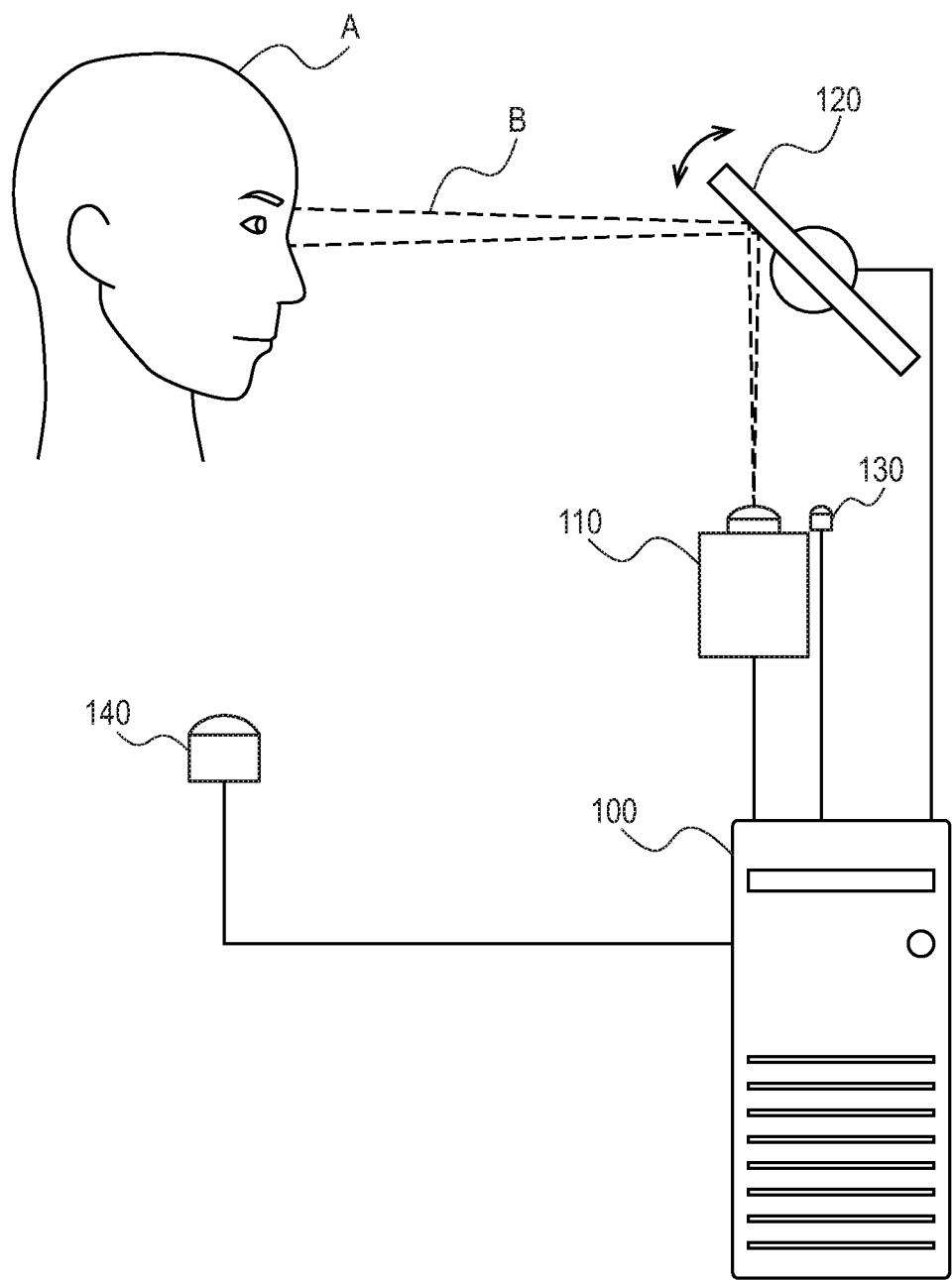
FIG. 1 is a schematic diagram of an iris capture apparatus according to a first example embodiment.

FIG. 1 is a schematic diagram of an iris capture apparatus 100 according to the present example embodiment. The iris capture apparatus 100 has a camera 110 that captures an iris of a user A, a rotatable movable mirror 120, a light source 130 that irradiates the user A with a light, and a human sensor 140 that detects the presence of the user A.

The camera 110 is a capture unit that performs capturing by using a reflected light B emitted to the user A from the light source 130 and reflected by the user A and outputs an image of a capture result as digital data. As the camera 110, any capture apparatus such as a Charge Coupled Device (CCD) camera, a Complementary Metal Oxide Semiconductor (CMOS) camera, or the like may be used. The camera 110 includes an image pickup device, an electric circuit, a lens, or the like that are necessary for capturing. The camera 110 is a narrow angle camera and is adjusted to capture a region of a part of the face of the user A at once via the movable mirror 120.

The light source 130 is a Light Emitting Diode (LED) that generates an infrared ray (having a wavelength of 0.7 μm to 1.0 mm) in the present example embodiment. The light source 130 irradiates the user A with an infrared ray when performing capturing by the camera 110. The light source 130 is provided near the lens of the camera 110, and the light from the light source 130 is emitted to the user A via the movable mirror 120. Any number of the light sources 130 may be provided, and it is desirable that a plurality of light sources 130 be provided so as to surround the side face of the lens of the camera 110. Further, the light source 130 may be provided at any position between the camera 110 and the mirror 120 without being limited to being provided near the camera 110. Alternatively, the light source 130 may be provided between the mirror 120 and the user A. As the light source 130, any light source such as a laser diode (LD), a lamp, or the like may be used without being limited to the LED. As a light irradiated to the user A by the light source 130, without being limited to an infrared ray, a light of any wavelength may be used in accordance with a purpose or an environment where iris capturing is performed.

The movable mirror 120 is provided on a light path of a light entering the camera 110. The movable mirror 120 is a mirror that guides a light from the light source 130 to the user A and further reflects the reflected light B, which is reflected on the user A, to guide the reflected light B to the lens of the camera 110. As the movable mirror 120, any optical system such as a plane mirror, a curved surface mirror, a prism, or the like that is capable of guiding the reflected light B to the lens of the camera 110 may be used.

The movable mirror 120 has a drive unit and rotates about a predetermined axis by being driven by the drive unit. The drive unit is a stepping motor in the present example embodiment. With the drive unit rotating the movable mirror 120, the capturing range on the user A taken by the camera 110 changes. That is, rotation of the movable mirror 120 enables the camera 110 to scan the entire region of the face of the user A.

The movable mirror 120 may be rotated about two or more axes without being limited to a single axis. As the drive unit of the movable mirror 120, any other drive units such as a motor, an actuator, or the like may be used as long as it can change the angle of the reflective surface of the movable mirror 120. Further, as the movable mirror 120, a galvanometer mirror may be used in which a mirror connected to a permanent magnet and an electromagnet provided facing the permanent magnet are used to control a current to the electromagnet and thereby the mirror can be rotated at a high speed.

The human sensor 140 is a sensor that detects the user A being present within a capturing range of the camera 110. The iris capture apparatus 100 can start capturing an iris in response to the presence of the user A being detected by the human sensor 140. As the human sensor 140, any sensor capable of detecting the presence of a human, such as an infrared sensor, an ultrasonic wave sensor, or the like, may be used.

The iris capture apparatus 100 acquires an iris image of the user A using an iris image acquisition method described later by capturing a face of the user A using the camera 110 while rotating the movable mirror 120.

Figure 2:
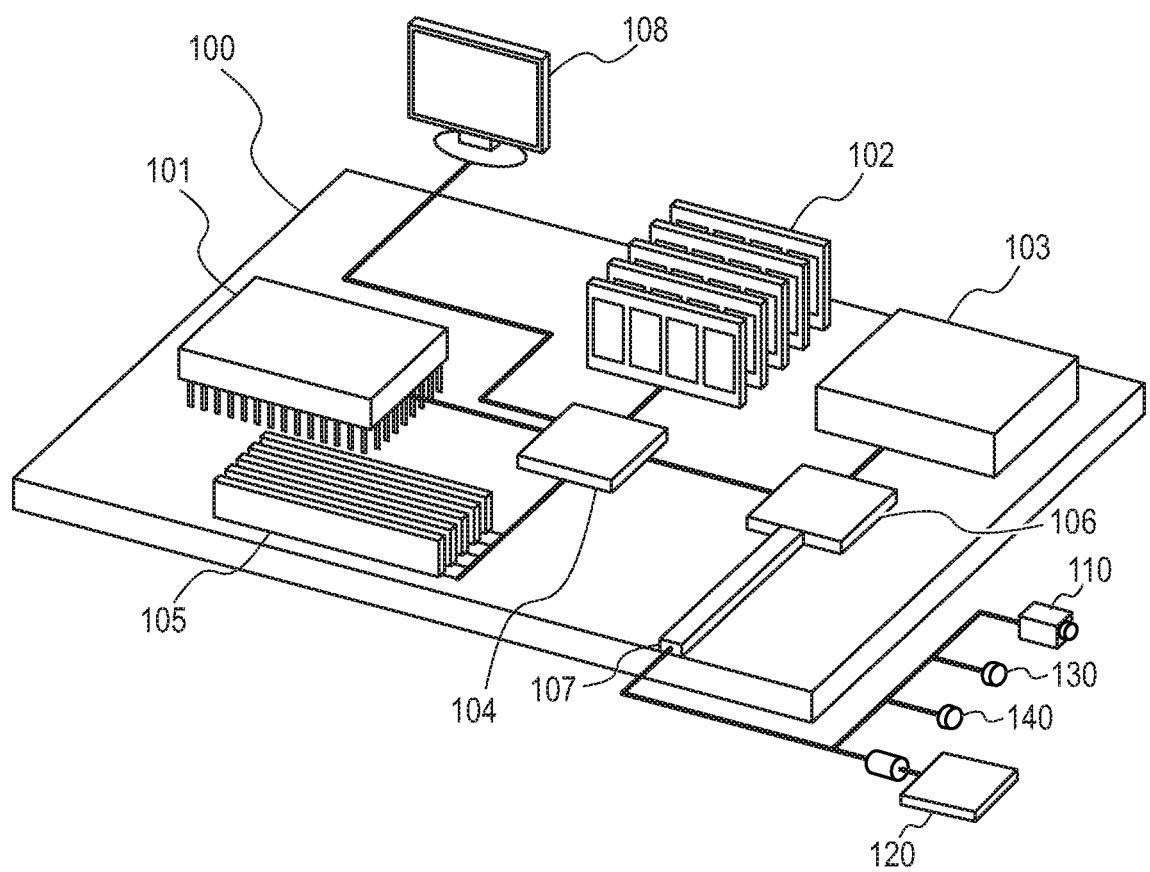
FIG. 2 is a schematic configuration diagram of the iris capture apparatus according to the first example embodiment.

FIG. 2 is a schematic configuration diagram of the iris capture apparatus 100 according to the present example embodiment. The iris capture apparatus 100 may be formed of a single apparatus or may be formed by two or more physically divided apparatuses connected by a wire or wirelessly. For example, the iris capture apparatus 100 may be a laptop computer, a desktop computer, a workstation, a personal digital assistant, a server, a blade server, a mainframe, an embedded system, or the like. The specific hardware configuration of the iris capture apparatus 100 is not limited to the configuration below but may be of various types or forms.

The iris capture apparatus 100 has a processor 101, a memory 102, and a storage device 103. Further, the iris capture apparatus 100 has a high-speed controller 104 including a high-speed interface and a low-speed controller 106 including a low-speed interface. The memory 102 and a high-speed expansion port 105 are connected to the high-speed controller 104. Further, a display device such as a display 108 is connected to the high-speed controller 104. On the other hand, a low-speed expansion port 107 and the storage device 103 are connected to the low-speed controller 106.

The processor 101, the memory 102, the storage device 103, the high-speed controller 104, the low-speed controller 106, and the high-speed expansion port 105 are connected to each other through various buses. Further, the processor 101, the memory 102, the storage device 103, the high-speed controller 104, the low-speed controller 106, and the high-speed expansion port 105 may be implemented on a common motherboard or may be implemented in other forms as appropriate.

The processor 101 is a central processing unit (CPU), for example, and is able to process instructions executed within the iris capture apparatus 100. Such instructions include an instruction that is used for displaying graphics information of a graphical user interface (GUI) on a display device such as the display 108 and stored in the memory 102 or the storage device 103.

Further, a plurality of processors, a plurality of busses, or a plurality of processors and a plurality of busses can be used as appropriate together with a plurality of memory devices and multiple types of memory devices. Further, a plurality of iris capture apparatuses 100 can be connected to each device that performs a part of the necessary process. For example, a plurality of iris capture apparatuses 100 can be connected to each other as a server bank, a group of blade servers, or a multiprocessor system.

The memory 102 stores therein information within the iris capture apparatus 100. For example, the memory 102 may be a volatile memory unit, a non-volatile memory unit, or the combination thereof. The memory 102 may be another computer readable storage medium, such as a magnetic disk, an optical disk, or the like, for example.

The storage device 103 can configure mass storage used for the iris capture apparatus 100. The storage device 103 may be a computer readable storage medium or include such a computer readable storage medium such as, for example, a floppy (registered trademark) disk device, a hard disk device, an optical disk device, a tape device, a solid state memory device such as a flash memory, a disk array, or the like. The storage device 103 may include a storage area network or may be a device with another configuration.

The high-speed controller 104 manages processes in which the bandwidth for the iris capture apparatus 100 is intensively used. On the other hand, the low-speed controller 106 manages processes in which the bandwidth is less intensively used. However, such allocation of the functions is a mere example, and allocation is not limited thereto. Further, a part or a whole of the high-speed controller 104 may be incorporated in the processor 101.

The high-speed controller 104 is connected to the high-speed expansion port 105 that can accept the memory 102 and various expansion cards. Further, the high-speed controller 104 is connected to the display 108 via a graphics processor or an accelerator, for example.

The low-speed controller 106 is connected to the storage device 103 and the low-speed expansion port 107. The low-speed expansion port 107 can include, for example, a communication port of various standards such as Universal Serial Bus (USB), Bluetooth (registered trademark), wired or wireless Ethernet (registered trademark), or the like. One or plurality of input devices such as a keyboard, a pointing device, a scanner, or the like are connected to the low-speed expansion port 107. Furthermore, the camera 110, the movable mirror 120, the light source 130 and the human sensor 140 described above are connected to the low-speed expansion port 107. Further, one or plurality of network devices such as a switch, a router, or the like can be connected to the low-speed expansion port 107 via a network adapter, for example. That is, the low-speed expansion port 107 functions as a communication interface.

The iris capture apparatus 100 can be implemented in many different forms without being limited to the form described above. For example, the iris capture apparatus 100 can be implemented in a form of a typical server or a plurality of servers in a form of a group of such servers. Further, the iris capture apparatus 100 can be implemented as a part of the rack server system. Furthermore, the iris capture apparatus 100 can be implemented in a form of a personal computer such as a laptop computer, a desktop computer, or the like.

Note that a part or a whole of the program executed by the processor 101 of the iris capture apparatus 100 can be provided by a computer readable storage medium storing the above, such as a digital versatile disc-read only memory (DVD-ROM), a compact disc-read only memory (CD-ROM), a flash memory such as a USB memory or the like.

Figure 3:
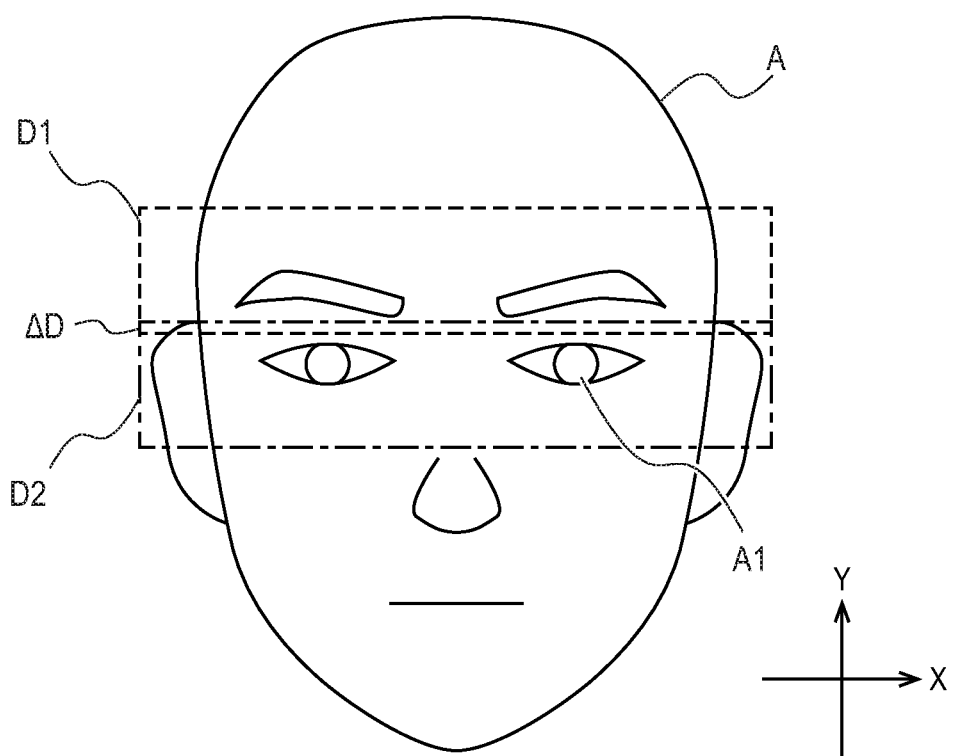
FIG. 3 is a schematic diagram a capture method performed by the iris capture apparatus according to the first example embodiment.

FIG. 3 is a schematic diagram of a capture method performed by the iris capture apparatus 100 according to the present example embodiment. FIG. 3 is a diagram of the face of the user A when viewed from the front. In FIG. 3, the gravity direction is defined as a Y-axis, and a direction perpendicular to the gravity direction is defined as an X-axis. The movable mirror 120 is adjusted so as to rotate about the X-axis. The camera 110 captures a capturing region D1 including a part of the face of the user A at once. In response to the movable mirror 120 being rotated by a predetermined angle from the state of the capturing region D1, the camera 110 captures a capturing region D2 moved by a predetermined distance in the Y-axis direction. The camera 110 captures the entire region of the face of the user A by rotating the movable mirror 120 for a predetermined number of times to perform capturing for the predetermined number of times. The iris capture apparatus 100 then detects an iris A1 of the user A from a group of captured images and acquires an iris image.

Each of the capturing regions D1 and D2 is a rectangular region that is longer in the X-axis direction (the horizontal direction with respect to a face) than in the Y-axis direction (the vertical direction with respect to a face). The camera 110 and the movable mirror 120 are arranged such that the vertical length of the capturing regions D1 and D2 is shorter than the vertical length of a face of the user A and the horizontal length of the capturing regions D1 and D2 is longer than the horizontal length of a face of the user A. As a size of a face of the user A, a preset size of a face of an average person may be used. With such a configuration, the camera 110 is able to scan vertically a face of the user A who may have various heights and capture the entire region only by rotating the movable mirror 120 about a single axis (X-axis). Further, since the vertical length of the capturing regions D1 and D2 is limited, it is possible to capture a high resolution iris image while suppressing a resolution required for the image pickup device of the camera 110.

In the neighboring capturing regions D1 and D2, an overlapping region ΔD where the capturing regions D1 and D2 overlap with each other for a predetermined length in the vertical direction is formed. With the overlapping region ΔD being provided in such a way, since the probability of the entire image of the iris A1 being included in at least one of the neighboring capturing regions D1 and D2 is increased, this can reduce the probability of the iris A1 being divided and no iris image being obtained. It is desirable that the length of the overlapping region ΔD be longer than or equal to half the vertical length of each of the capturing regions D1 and D2. Thereby, since each point on the face of the user A is included in both the capturing regions D1 and D2 neighboring each other, it is possible to effectively suppress the iris A1 from being divided.

For example, when the camera 110 having a view angle of 11 degrees is used and when the distance between the camera 110 and the movable mirror 120 is 5 cm and the distance between the movable mirror 120 and the user A is 30 cm, the vertical length of the capturing regions D1 and D2 will be 2×tan(11/2)×(30+5)=6.7 cm. Since the vertical length of a face of an average person is around 21 cm to 24 cm, an iris image of the user A can be acquired by performing rotation and capturing for around six times even taking the overlapping region into consideration. The size of the capturing regions D1 and D2 may be set in accordance with the arrangement or the capture environment of the iris capture apparatus 100.

Figure 4:
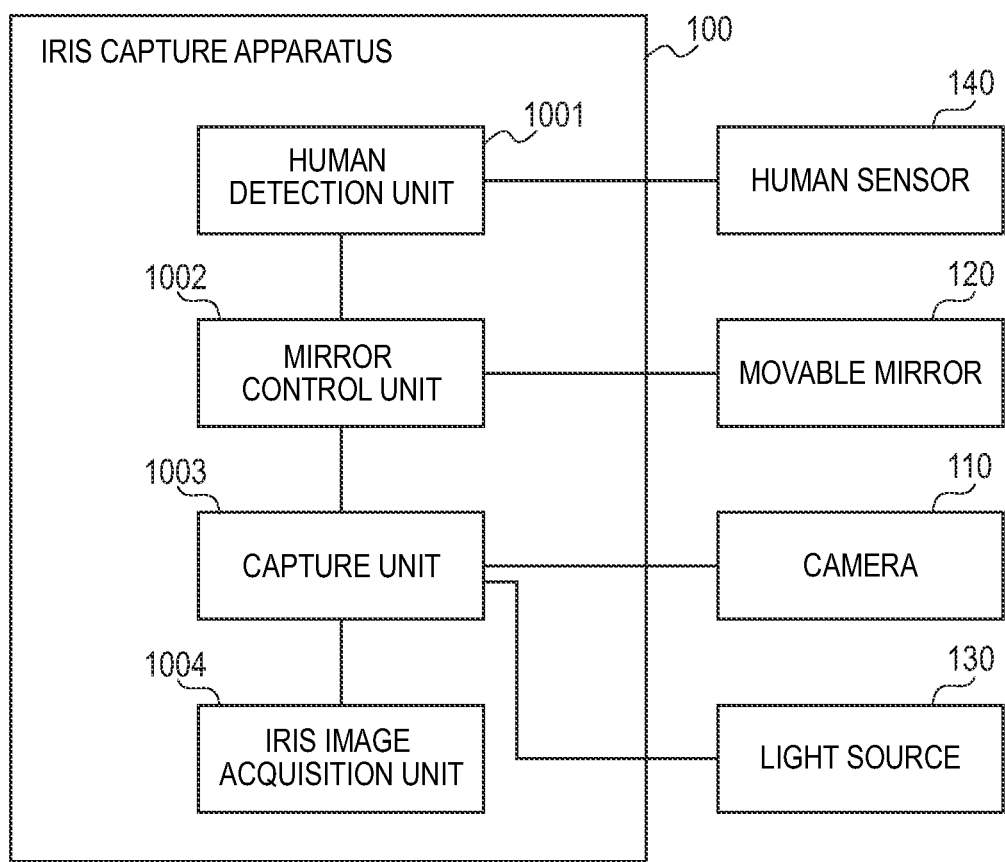
FIG. 4 is a block diagram of the iris capture apparatus according to the first example embodiment.

FIG. 4 is a block diagram of the iris capture apparatus 100 according to the present example embodiment. In FIG. 4, lines between blocks illustrate main dataflows, and other dataflows than is illustrated in FIG. 4 may be provided. In FIG. 4, each block does not illustrate a configuration of a hardware (device) unit but illustrates a configuration of a function unit.

The iris capture apparatus 100 has a human detection unit 1001, a mirror control unit 1002, a capture unit 1003, and an iris image acquisition unit 1004. In the iris capture apparatus 100, the human detection unit 1001, the mirror control unit 1002, the capture unit 1003, and the iris image acquisition unit 1004 are stored in the memory 102 as programs executable by the processor 101, respectively. That is, when the iris capture method according to the present example embodiment is executed, the processor 101 functions as the human detection unit 1001, the mirror control unit 1002, the capture unit 1003, and the iris image acquisition unit 1004. At least some of these functions may be implemented as an electronic circuit rather than a program.

The human detection unit 1001 uses the human sensor 140 to detects whether or not the user A is present within a capturing range of the camera 110 every predetermined time (for example, every 0.1 second). The human detection unit 1001 holds the latest detection result in the memory 102 or the storage device 103. Based on the result detected by the human detection unit 1001, the mirror control unit 1002, the capture unit 1003, and the iris image acquisition unit 1004 start capturing an iris when the user A is present.

The mirror control unit 1002 and the capture unit 1003 cause the camera 110 to capture images of the face of the user A while rotating the movable mirror 120. First, the mirror control unit 1002 transmits an electrical signal to the movable mirror 120 and drives the movable mirror 120 to rotate up to a predetermined start position. Next, the capture unit 1003 irradiates the user A with a light from the light source 130 and causes the camera 110 to capture a predetermined capturing range on the user A. Every time capturing is performed by the capture unit 1003, the mirror control unit 1002 transmits an electrical signal to the movable mirror 120 and drives the movable mirror 120 to rotate by a predetermined angle. In such a way, rotation operated by the mirror control unit 1002 and capturing operated by the capture unit 1003 are repeated. After rotation operated by the mirror control unit 1002 and capturing operated by the capture unit 1003 are repeated for a predetermined number of times, the capture unit 1003 holds a group of captured images in the memory 102 or the storage device 103 and ends the capturing. The start position of the movable mirror 120 and the angle and the number of repetition of the rotation of the movable mirror 120 are preset in accordance with the arrangement of the camera 110 and the movable mirror 120 and stored in the storage device 103. It is desirable that the angle of one time of rotation of the movable mirror 120 be smaller than or equal to 7.5 degrees.

Furthermore, the number of repetition of rotation of the movable mirror 120 may be dynamically determined based on the position of the user A. In this case, the human detection unit 1001 uses the human sensor 140 to measure the distance to the user A. The mirror control unit 1002 then determines the number of repetition of rotation of the movable mirror 120 based on the distance measured by the human detection unit 1001. This is because the size of the capturing region on the user A changes depending on the distance from the camera 110 even when the movable mirror 120 is rotated by the same angle. For example, the mirror control unit 1002 decreases the number of repetition of rotation of the movable mirror 120 when the user A is located distant and increases the number of repetition of rotation of the movable mirror 120 when the user A is located close. With such a configuration, a region including the upper end to the lower end of the face of the user A can be captured by the appropriate number of times.

The iris image acquisition unit 1004 acquires an iris image from a group of images acquired by the capture unit 1003. Acquisition of an iris image from a group of images is performed by either a division image scheme of selecting an image including an iris from a group of images to extract the iris or a composite image scheme of creating a composite image from a group of images to extract an iris. Respective schemes will be described below.

Figure 5:
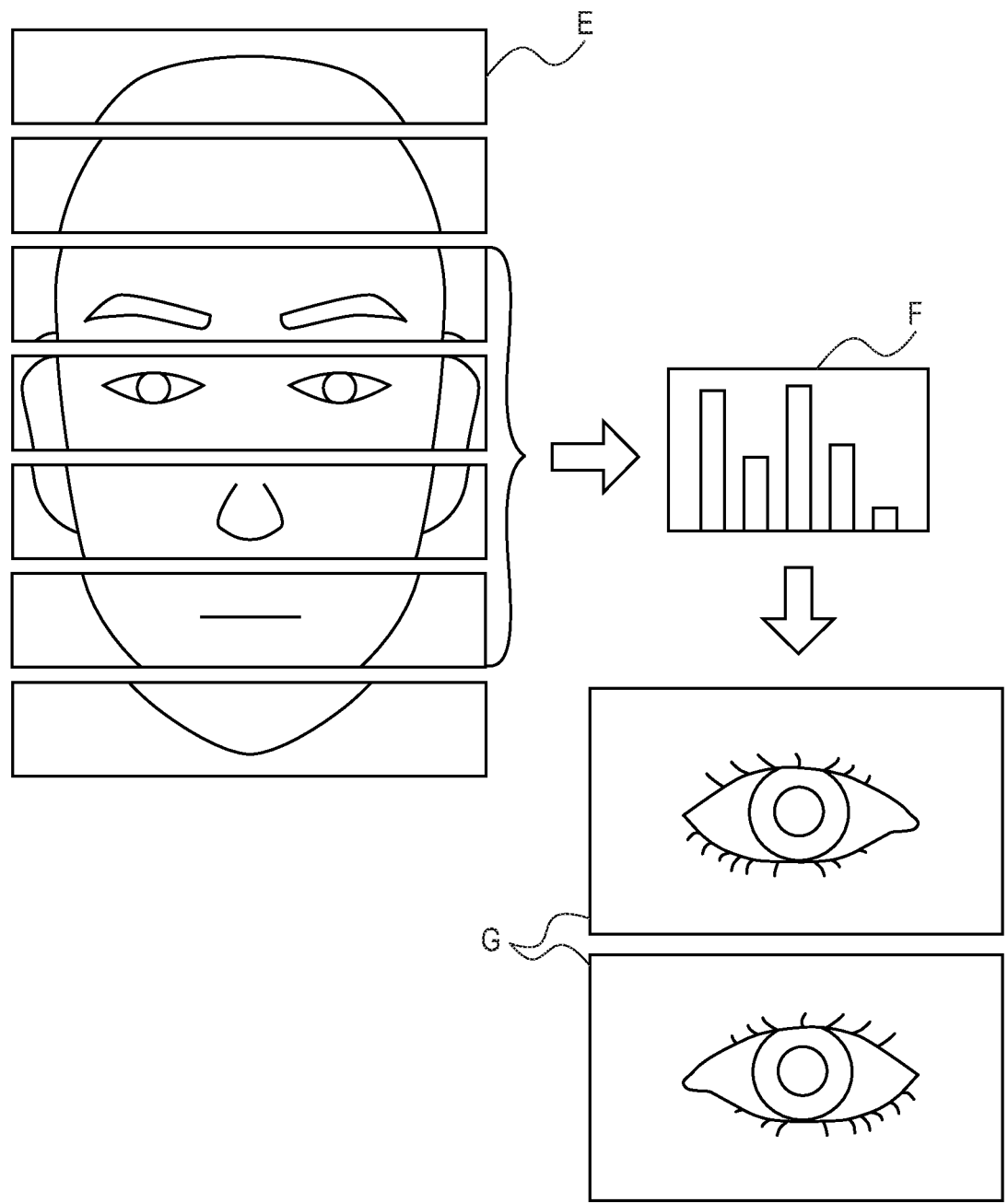
FIG. 5 is a schematic diagram of an iris image acquisition method of a division image scheme according to the first example embodiment.

FIG. 5 is a schematic diagram of an iris image acquisition method of the division image scheme according to the present example embodiment. First, the iris image acquisition unit 1004 acquires a group of divided images E captured by the capture unit 1003 from the memory 102 or the storage device 103. The divided images E are obtained by capturing respective different regions on the user A. Next, the iris image acquisition unit 1004 performs coarse search of the divided images E for a face region and selects images including the face region. The coarse search for a face region is performed based on the relative positional relationship between components of a face, such as an eyebrow(s), an eye(s), a nose, a mouth, or the like. For example, the coarse positions of an eyebrow(s) and a mouth are acquired by using template matching from the divided images E, the divided image E including the eyebrow(s) to the divided image E including the mouth are selected, and the selected divided images E are a detection target of an iris. The coarse search for a face region may be omitted, and all the divided images E may be the detection target of an iris.

Next, the iris image acquisition unit 1004 calculates a feature amount F for each predetermined range about each point of the divided image E that is the detection target of an iris. The range used for calculation of the feature amount F has a size sufficient to include an iris. The iris image acquisition unit 1004 then calculates a similarity of the feature amount F at each point with respect to a feature amount of a pre-stored iris and detects, as the position of the iris, a point at which the similarity is greater than or equal to a predetermined threshold. When a plurality of points where the similarity is greater than or equal to a predetermined threshold are detected, the point at which the similarity is the highest may be determined as an iris. Detection of an iris is performed for both left and right eyes, respectively. The feature amount F may be calculated by using a known method for identifying a component of a face. A feature amount of an iris to be compared to the feature amount F of the divided image E is calculated in advance from an image of an average iris and stored in the storage device 103. The threshold of the similarity is determined in advance through an experiment or a simulation and stored in the storage device 103.

Finally, the iris image acquisition unit 1004 cuts out predetermined ranges each including the position of the detected iris as iris images G for left and right eyes, respectively, from the divided image E and holds the iris mages G in the memory 102 or the storage device 103. The range of the iris image G may have a size including only the iris or may have a size including the entire eye.

Figure 6:
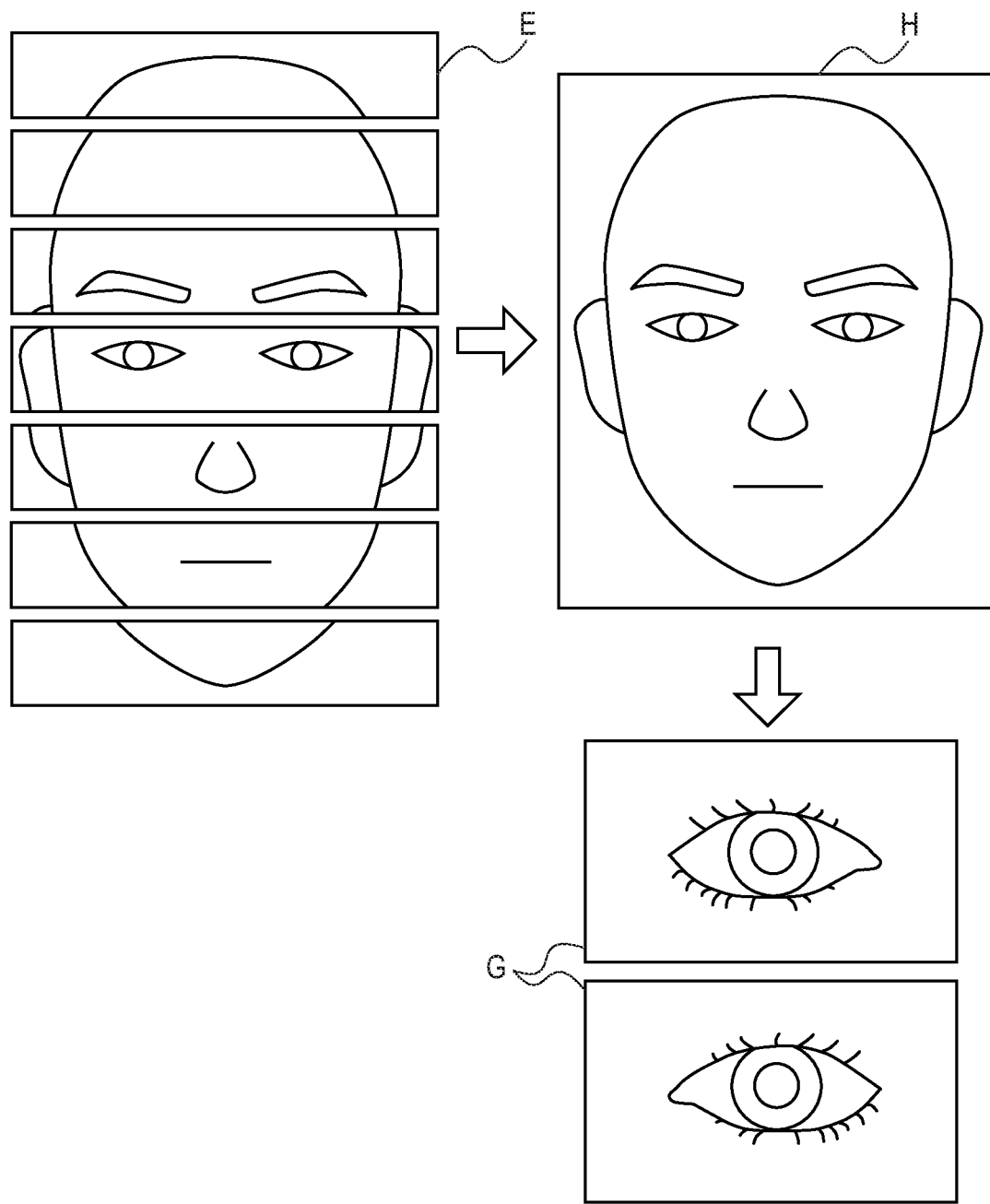
FIG. 6 is a schematic diagram of an iris image acquisition method of a composite image scheme according to the first example embodiment.

FIG. 6 is a schematic diagram of an iris image acquisition method of the composite image scheme according to the present example embodiment. First, the iris image acquisition unit 1004 acquires a group of divided images E captured by the capture unit 1003 from the memory 102 or the storage device 103. The divided images E are obtained by capturing respective different regions on the user A. Next, the iris image acquisition unit 1004 generates a single composite image H from the divided images E so as to exclude the overlapping regions ΔD in FIG. 3. For example, the composite image H is generated by deleting portions corresponding to the vertical lengths of overlapping regions ΔD from respective lower ends (or upper ends) of respective divided images and then connecting the divided images E to each other in the vertical direction.

The iris image acquisition unit 1004 then determines the position of eyes from the composite image H by using a known face recognition method. Finally, the iris image acquisition unit 1004 cuts out, as iris images G, predetermined ranges including respective positions of the detected left and right eyes from the composite image H and holds the iris mages G in the memory 102 or the storage device 103. The range of the iris image G may have a size including only the iris or may have a size including the entire eye.

In the iris image acquisition method of the division image scheme, there is an advantage that, even when the full face of the user A is not generated from composite images due to motion of the face during capturing or the like, an iris image can be acquired as long as an iris is included in any of the divided images E. On the other hand, in the iris image acquisition method of the composite image scheme, there is an advantage that, since the position of the eye can be detected based on the arrangement of components of the entire face, an accurate iris image can be acquired. As an iris image acquisition method, any of the division image scheme and the composite image scheme may be used, or both of them may be used in combination. As an iris image acquisition method, any method that can acquire an image of an iris from an image of a face may be used without being limited to the above schemes.

Figure 7:
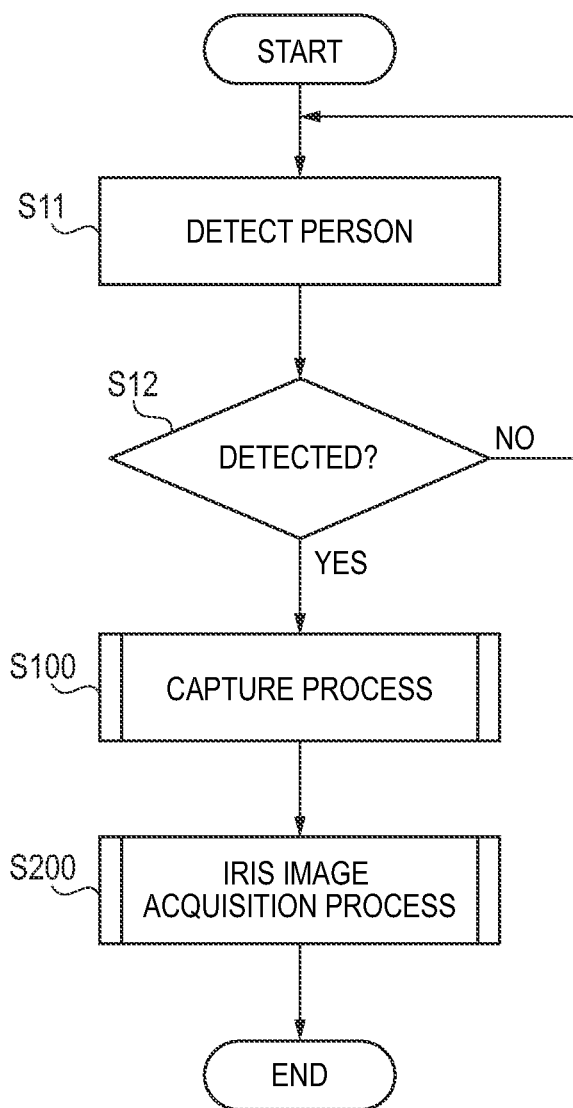
FIG. 7 is a diagram illustrating a flowchart of an iris image capture method according to the first example embodiment.

FIG. 7 is a diagram illustrating a flowchart of the iris capture method according to the present example embodiment. First, the human detection unit 1001 uses the human sensor 140 to detect whether or not the user A is present within the capturing range of the camera 110 (step S11). If the user A is not detected in step S11 (step S12, NO), step S11 is repeated every predetermined time. If the user A is detected in step S11 (step S12, YES), the iris capture apparatus 100 acquires an image of a face of the user A using a capture process described later by using FIG. 8 (step S100). Finally, the iris capture apparatus 100 acquires an iris image of the user A using an iris image acquisition process described later by using FIG. 9 and FIG. 10 from the image of the face of the user A acquired in step S100 (step S200). The iris image acquisition process is implemented with at least one of the division image scheme and the composite image scheme.

Figure 8:
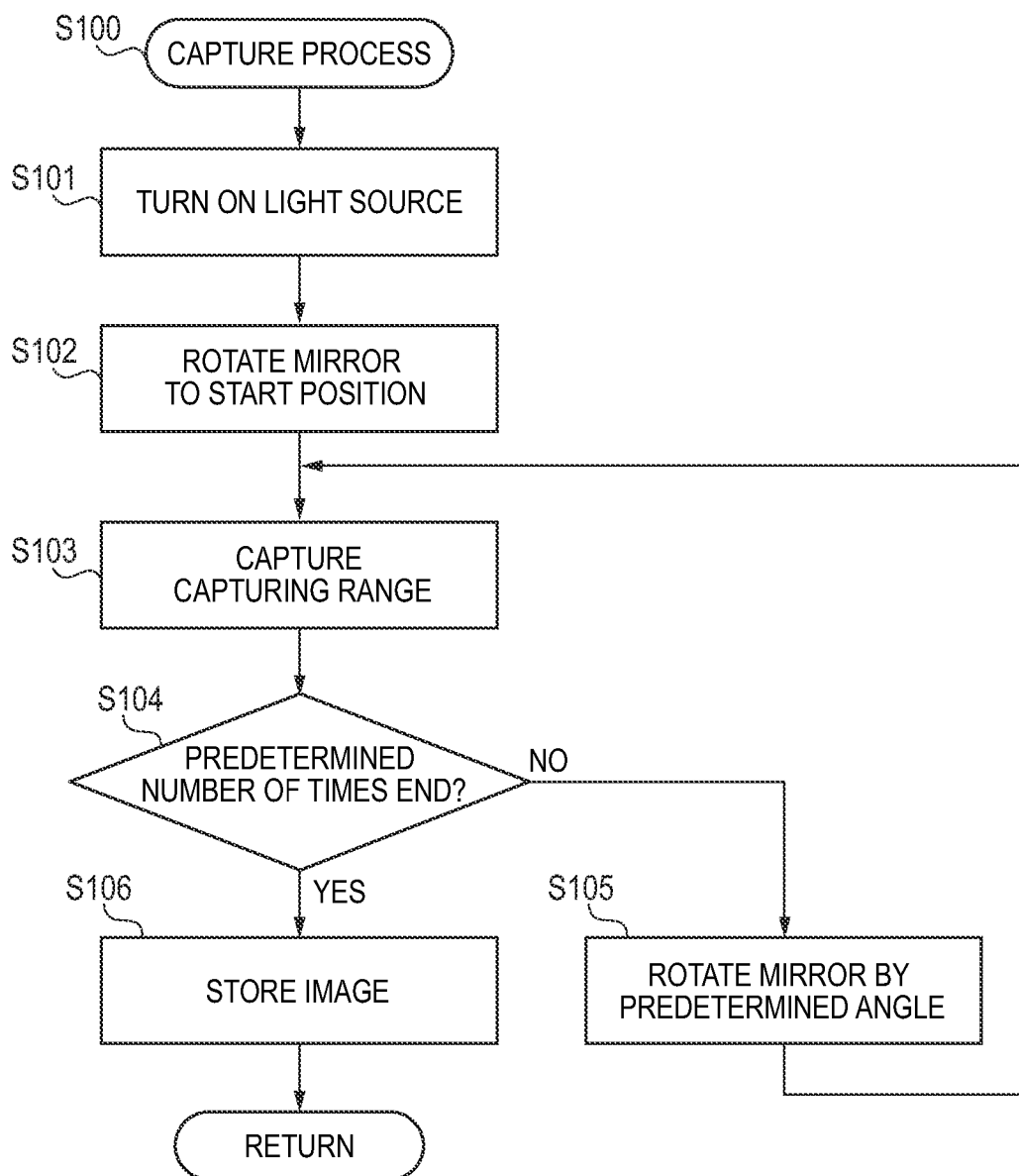
FIG. 8 is a diagram illustrating a flowchart of a capture process according to the first example embodiment.

FIG. 8 is a diagram illustrating a flowchart of a capture process according to the present example embodiment. First, the capture unit 1003 turns on the light source 130 to irradiate the user A with a light (step S101). The light source 130 may be turned on all the time during a capture process or may be turned on intermittently only during capturing being performed by the camera 110. Next, the mirror control unit 1002 drives the movable mirror 120 and rotates the movable mirror 120 up to a predetermined start position (step S102). Next, the capture unit 1003 causes the camera 110 to capture a predetermined capturing range on the user A (step S103). If a predetermined number of times of capturing is not completed (step S104, NO), the mirror control unit 1002 drives the movable mirror 120 and rotates the movable mirror 120 by a predetermined angle (step S105). Steps S103 to S105 are repeated until the number of times of capturing reaches the predetermined number of times.

If the predetermined number of times of capturing ends (step S104, YES), the capture unit 1003 stores a group of images captured in steps S103 to S105 in the memory 102 or the storage device 103 (step S106). The iris capture apparatus 100 then ends the capture process.

Figure 9:
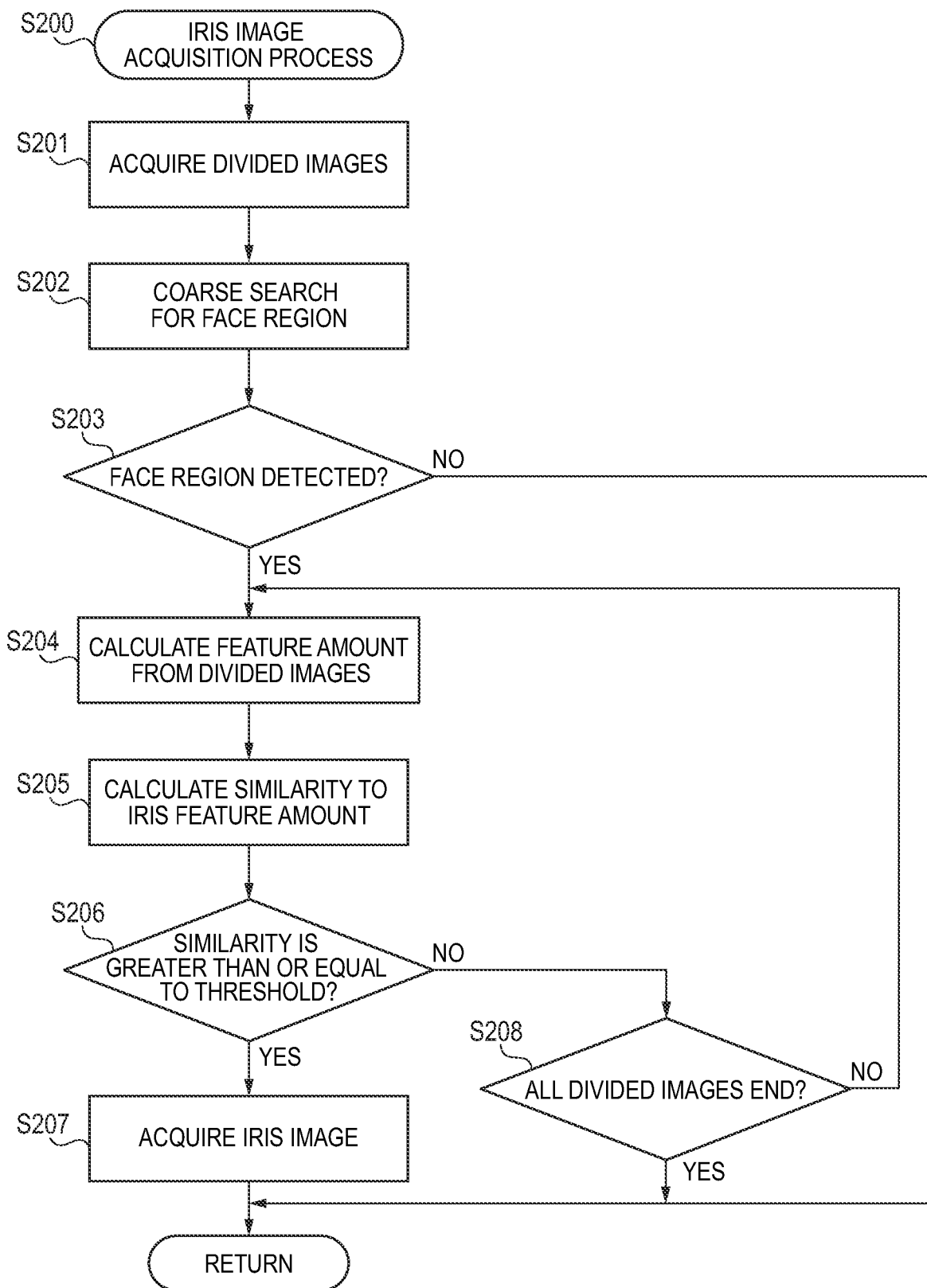
FIG. 9 is a diagram illustrating a flowchart of an iris image acquisition process of a division image scheme according to the first example embodiment.

FIG. 9 is a diagram illustrating a flowchart of the iris image acquisition process of the division image scheme according to the present example embodiment. First, the iris image acquisition unit 1004 reads a group of images captured in the capture process of step S100 from the memory 102 or the storage device 103 and acquires the read images as the divided images E (step S201). Next, the iris image acquisition unit 1004 performs coarse search for a face region on the divided images E acquired in step S201 and selects images including the face region out of the divided images E (step S202). If no face region is detected in step S202 (step S203, NO), the iris capture apparatus 100 outputs an indication that no iris image has been acquired and ends the iris image acquisition process.

If a face region is detected in step S202 (step S203, YES), the iris image acquisition unit 1004 calculates a feature amount for each predetermined range about each point within one of the divided images E including the face region selected in step S202 (step S204). The iris image acquisition unit 1004 then calculates a similarity of a feature amount of each point calculated in step S204 with respect to a feature amount of a pre-stored iris (step S205). If there is no point at which the similarity calculated in step S205 is greater than or equal to a predetermined threshold (step S206, NO) and if the process is not completed for all the divided images E including the face region selected in step S202 (step S208, NO), steps S204 to S206 are performed for the next one divided image E. If there is no point at which the similarity calculated in step S205 is greater than or equal to a predetermined threshold (step S206, NO) and if the process is completed for all the divided images E including the face region selected in step S202 (step S208, YES), the iris capture apparatus 100 outputs an indication that no iris image has been acquired and ends the iris image acquisition process.

If there is a point at which the similarity calculated in step S205 is greater than or equal to a predetermined threshold (step S206, YES), the iris image acquisition unit 1004 cuts out a predetermined range including the point from the divided image E and stores the cut out predetermined ranges as the iris image G in the memory 102 or the storage device 103 (step S207). Acquisition of the iris image G is performed for both left and right eyes, respectively. The iris capture apparatus 100 then ends the iris image acquisition process.

Figure 10:
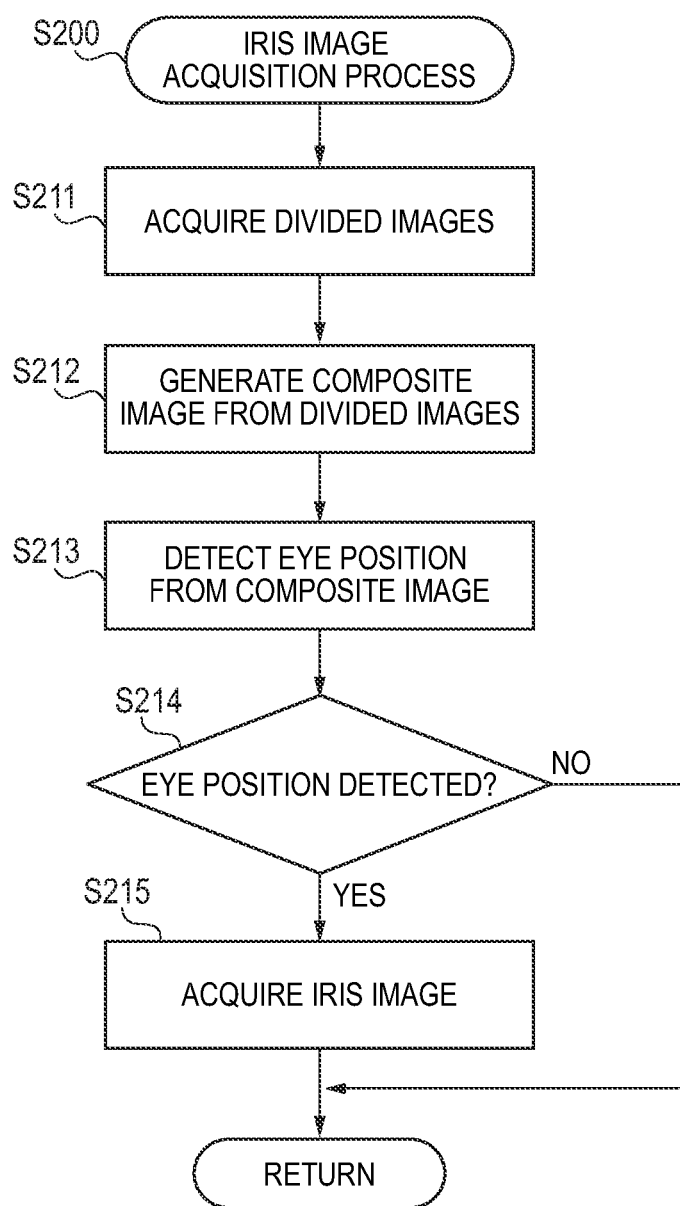
FIG. 10 is a diagram illustrating a flowchart of an iris image acquisition process of a composite image scheme according to the first example embodiment.

FIG. 10 is a diagram illustrating a flowchart of an iris image acquisition process of the composite image scheme according to the present example embodiment. First, the iris image acquisition unit 1004 reads a group of images captured in the capture process of step S100 from the memory 102 or the storage device 103 and acquires the read images as the divided images E (step S211). Next, the iris image acquisition unit 1004 composes the divided images E acquired in step S211 to generate the composite image H (step S212). The iris image acquisition unit 1004 detects the positions of the eyes from the composite image H generated in step S212 by using a known face recognition method (step S213). If the positions of the eyes are not detected in step S213 (step S214, NO), the iris capture apparatus 100 outputs an indication that no iris image has been acquired and ends the iris image acquisition process.

If the positions of the eyes are detected in step S213 (step S214, YES), the iris image acquisition unit 1004 cuts out predetermined ranges including the detected positions of the eyes as the iris images G from the composite image H and holds the cut out predetermined ranges as the iris image G in the memory 102 or the storage device 103 (step S215). Acquisition of the iris image G is performed for both left and right eyes, respectively. The iris capture apparatus 100 then ends the iris image acquisition process.

The processor 101 of the iris capture apparatus 100 is the subject of each step (operation) included in the process illustrated FIG. 8 to FIG. 10. That is, the processor 101 reads a program used for executing each of the processes illustrated in FIG. 8 to FIG. 10 from the memory 102 or the storage device 103, executes the program to control each unit of the iris capture apparatus 100, and thereby performs the process illustrated in FIG. 8 to FIG. 10.

The iris capture apparatus 100 according to the present example embodiment acquires a high resolution iris image by repeatedly capturing a part of the face of the user A while repeatedly rotating the movable mirror 120. Since the movable mirror 120 is lighter than the camera 110 in general, the torque at the drive unit used for rotating the movable mirror 120 is small. Thus, the iris capture apparatus 100 can shorten the time required for rotation and the time required for stop thereof compared to the case of rotating the camera 110 and quickly capture an iris. Further, the iris capture apparatus 100 can obtain a high resolution iris image by using only the single type of the camera 110 without requiring multiple types of cameras such as a wide angle camera and a telescope camera as disclosed in the arts of Patent Literatures 1 and 2. Thus, the iris capture apparatus 100 can quickly capture an iris and reduce manufacturing cost with a simple apparatus configuration.

Second Example Embodiment

Figure 11:
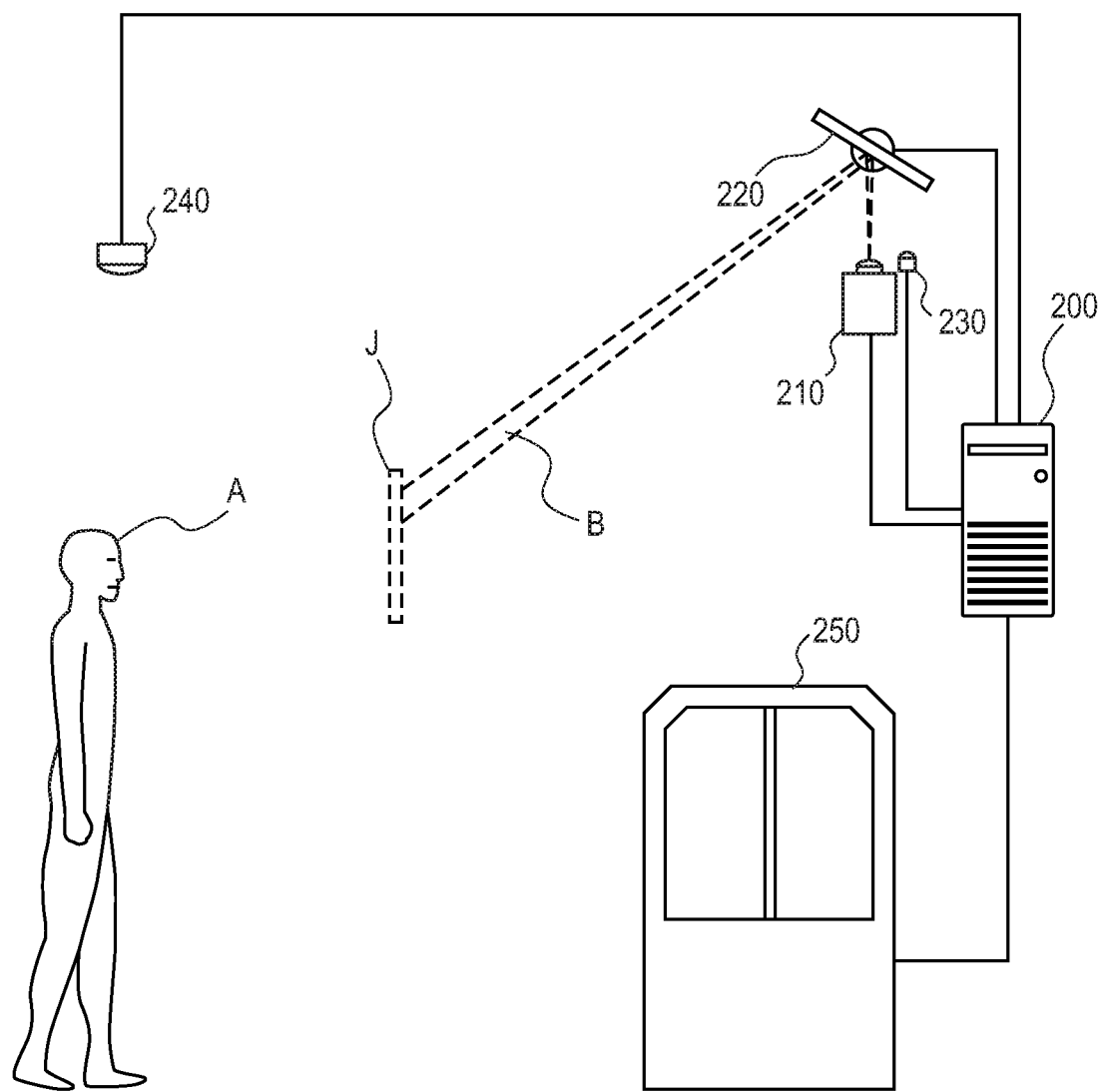
FIG. 11 is a schematic diagram of an iris capture apparatus according to a second example embodiment.

The present example embodiment performs walk-through recognition in which iris recognition is performed on the moving user A. FIG. 11 is a schematic diagram of an iris capture apparatus 200 according to the present example embodiment. The iris capture apparatus 200 has a camera 210, a movable mirror 220, a light source 230, a human sensor 240, and a gate 250.

The camera 210, the movable mirror 220, the light source 230, and the human sensor 240 are similar to the camera 110, the movable mirror 120, the light source 130, and the human sensor 140 according to the first example embodiment, respectively. The gate 250 is a gate that has a drive unit and can be opened and closed, and the opened state and the closed state can be switched by being driven by the drive unit.

While having a configuration common to the movable mirror 120 according to the first example embodiment, the movable mirror 220 is different in the feature of rotation about two axes. The movable mirror 220 rotates about two predetermined axes by being driven by the drive unit. That is, the iris capture apparatus 200 can change the capturing range not only in the vertical direction but also in the horizontal direction. As the movable mirror 220, two mirrors that are separately rotated may be used in combination rather than a single mirror. In such a case, the movable mirror 220 includes a first mirror that is rotated about a first axis and a second mirror that is rotated about a second axis that is different from the first axis. Further, the reflected light B from the user A enters the camera 210 via the first mirror and the second mirror.

The iris capture apparatus 200 repeatedly captures the inside of a predetermined scan region J by rotating the movable mirror 220. The scan region J is located in a space between the detecting range of the human sensor 240 and the gate 250. This enables the iris capture apparatus 200 to acquire an iris image of the user A at the timing when the moving user A enters the inside of the scan region J after detected by the human sensor 240.

Figure 12:
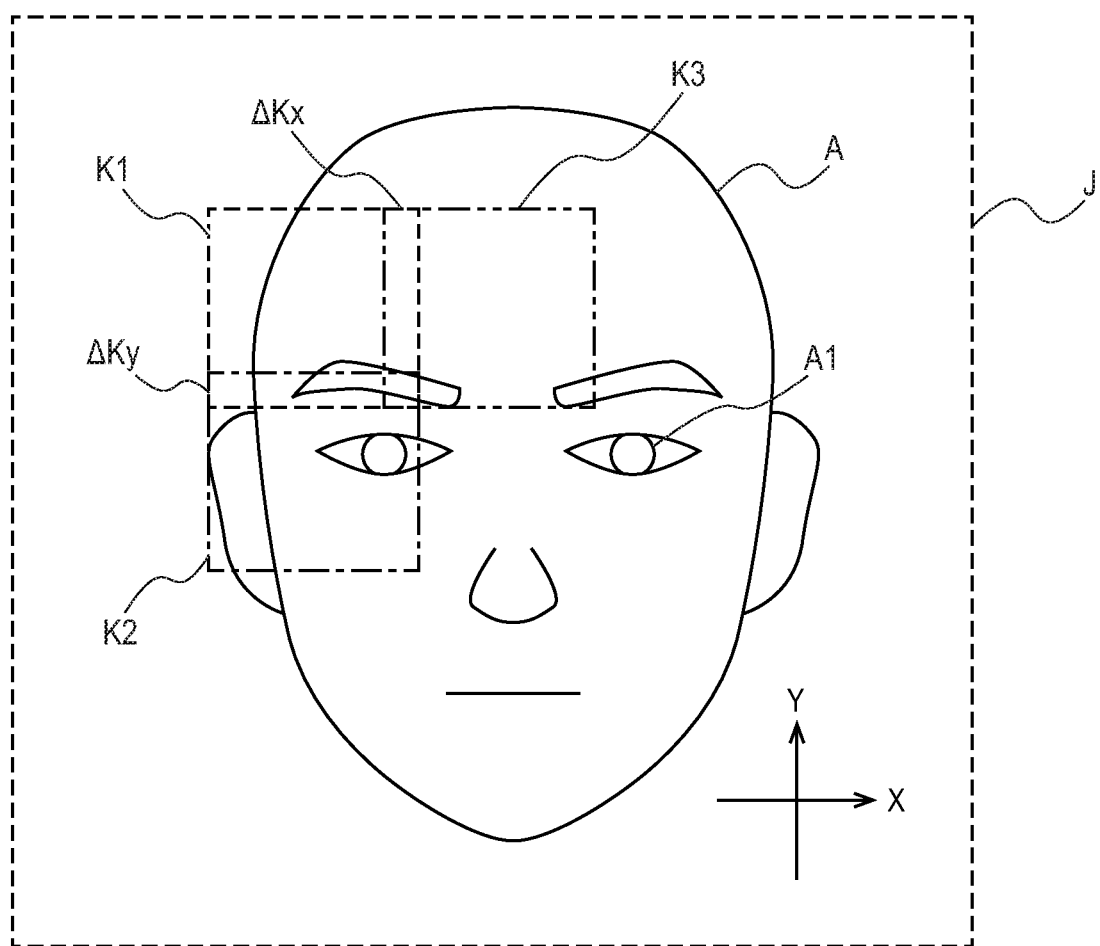
FIG. 12 is a schematic diagram of a capture method performed by the iris capture apparatus according to the second example embodiment.

FIG. 12 is a schematic diagram of a capture method performed by the iris capture apparatus 200 according to the present example embodiment. FIG. 12 is a diagram of the face of the user A when viewed from the front. In FIG. 12, the gravity direction is defined as a Y-axis, and a direction perpendicular to the gravity direction is defined as an X-axis. The movable mirror 220 is adjusted so as to rotate about the X-axis and the Y-axis. The camera 210 captures a capturing region K1 including a part of the face of the user A at once. In response to the movable mirror 220 being rotated by a predetermined angle about the X-axis from the state of the capturing region K1, the camera 210 captures a capturing region K2 moved by a predetermined distance in the Y-axis direction. In response to the movable mirror 220 being rotated by a predetermined angle about the Y-axis from the state of the capturing region K1, the camera 210 captures a capturing region K3 moved by a predetermined distance in the X-axis direction. The camera 210 captures the entire region within the scan region J by repeating capturing while rotating the movable mirror 220 about the X-axis or the Y-axis by a predetermined angle. The iris capture apparatus 200 then detects the iris A1 of the user A from a group of captured images and acquires an iris image. The sizes of the capturing regions K1 to K3 and the size of the scan region J may be set in accordance with the arrangement or the capture environment of the iris capture apparatus 200.

In the vertically neighboring capturing regions K1 and K2, an overlapping region ΔKy where the capturing regions K1 and K2 overlap with each other for a predetermined length in the vertical direction is formed. Further, in the horizontally neighboring capturing regions K1 and K3, an overlapping region ΔKx where the capturing regions K1 and K3 overlap with each other for a predetermined length in the horizontal direction is formed. With the overlapping regions ΔKx and ΔKy being provided in such a way, since the probability of the entire image of the iris A1 being included in at least one of the neighboring capturing regions K1 and K2 (or K3) is increased, this can reduce the probability of the iris A1 being divided and no iris image being obtained. It is desirable that the length of the overlapping region ΔKx be longer than or equal to half the horizontal length of each of the capturing regions K1 and K3. It is desirable that the length of the overlapping region ΔKy be longer than or equal to half the vertical length of each of the capturing regions K1 and K2. Thereby, since each point on the face of the user A is included in both the capturing regions K1 and K2 (or K3) neighboring each other, it is possible to effectively suppress the iris A1 from being divided.

While the movable mirror 220 according to the present example embodiment is rotated about two axes, the movable mirror 220 may be rotated about a single axis as with the first example embodiment. In such a case, the width in the horizontal direction of the capturing region K1 is equal to the width in the horizontal direction of the scan region J, the movable mirror 220 is rotated about one axis (X-axis), and thereby the entire scan region J can be captured.

Figure 13:
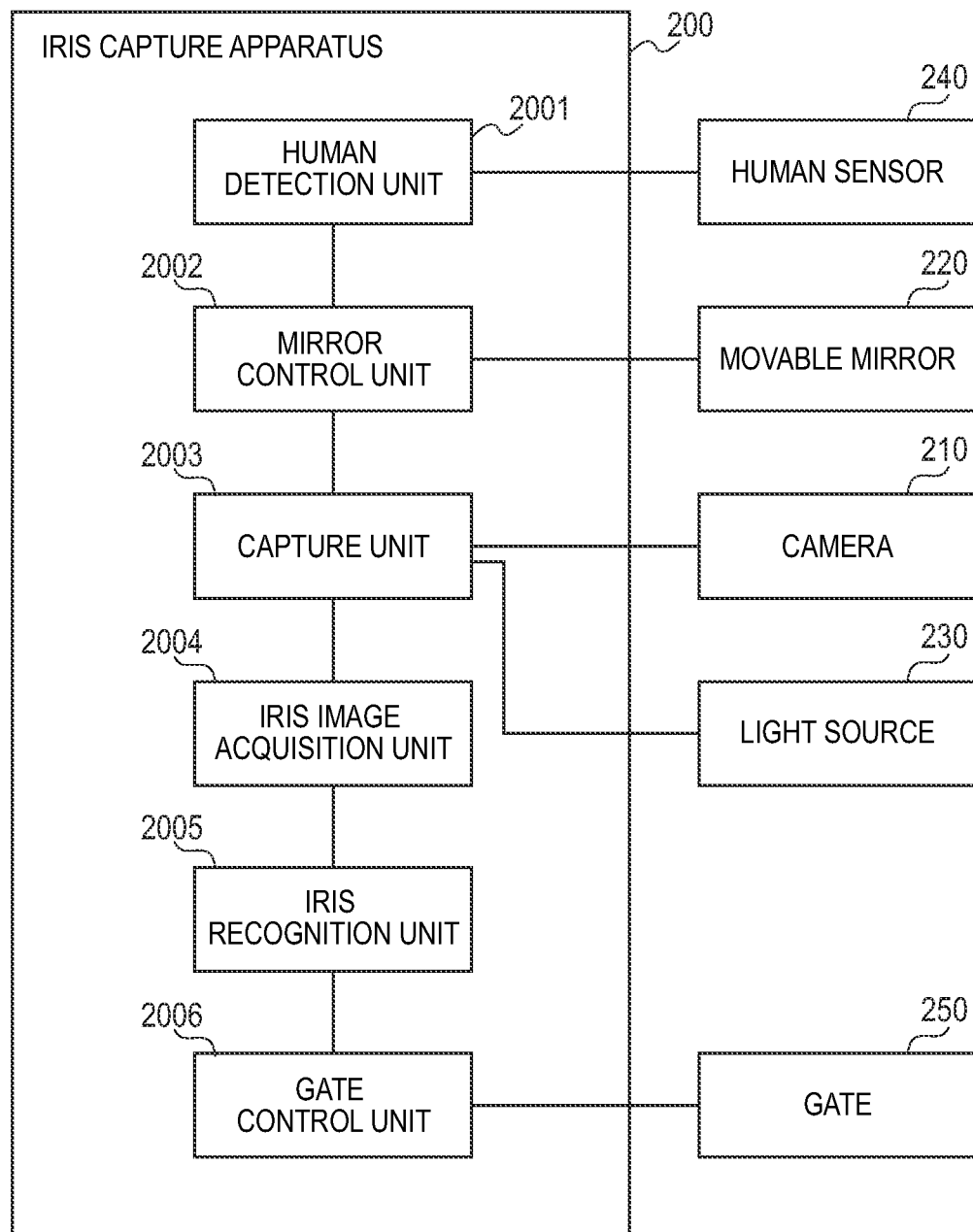
FIG. 13 is a block diagram of the iris capture apparatus according to the second example embodiment.

The apparatus configuration of the iris capture apparatus 200 is the same as the iris capture apparatus 100 illustrated in FIG. 2. FIG. 13 is a block diagram of the iris capture apparatus 200 according to the present example embodiment. In FIG. 13, lines between blocks illustrate main dataflows, and other dataflows than is illustrated in FIG. 13 may be provided. In FIG. 13, each block does not illustrate a configuration of a hardware (device) unit but illustrates a configuration of a function unit.

The iris capture apparatus 200 has a human detection unit 2001, a mirror control unit 2002, a capture unit 2003, an iris image acquisition unit 2004, an iris recognition unit 2005, and a gate control unit 2006. In the iris capture apparatus 100, the human detection unit 2001, the mirror control unit 2002, the capture unit 2003, the iris image acquisition unit 2004, the iris recognition unit 2005, and the gate control unit 2006 are stored in the memory 102 as programs executable by the processor 101, respectively. That is, when the iris capture method according to the present example embodiment is executed, the processor 101 functions as the human detection unit 2001, the mirror control unit 2002, the capture unit 2003, the iris image acquisition unit 2004, the iris recognition unit 2005, and the gate control unit 2006. At least some of these functions may be implemented by an electric circuit rather than a program.

The human detection unit 2001 uses the human sensor 240 to detect whether or not the user A is present within (that is, passes through) a predetermined detecting range every predetermined time (for example, every 0.1 second). The detecting range of the human sensor 240 is set in a space over a path on which the user A moves to the gate 250. The human detection unit 2001 holds the latest detection result in the memory 102 or the storage device 103. The mirror control unit 2002, the capture unit 2003, and the iris image acquisition unit 2004 repeat acquisition of an iris image during a predetermined period (for example, 5 seconds) after the presence of the user A is detected by the human detection unit 2001.

The mirror control unit 2002 and the capture unit 2003 cause the camera 210 to capture the scan region J, which is closer to the gate 250 than the detecting range of the human sensor 240 and is located in a space over a path on which the user A moves to the gate 250. First, the mirror control unit 2002 transmits an electrical signal to the movable mirror 220 and drives the movable mirror 220 to rotate up to a predetermined start position. Next, the capture unit 2003 emits a light from the light source 230 to the scan region J and causes the camera 210 to capture a predetermined capturing range within the scan region J. Every time capturing is performed by the capture unit 2003, the mirror control unit 2002 transmits an electrical signal to the movable mirror 220 and drives the movable mirror 220 to rotate by a predetermined direction. In such a way, rotation operated by the mirror control unit 2002 and capturing operated by the capture unit 2003 are repeated. After rotation operated by the mirror control unit 2002 and capturing operated by the capture unit 2003 are repeated for a predetermined number of times, the capture unit 2003 holds a captured group of images (that is, the entire image of the scan region J) in the memory 102 or the storage device 103 and acquires the next iris image. Until the iris image is successfully acquired or until a predetermined time has elapsed, the mirror control unit 2002 again drives the movable mirror 220 to move the movable mirror 220 back to the predetermined start position and repeats the capturing of an image of the scan region J to the acquisition of the iris image. The start position of the movable mirror 220 and the angle and the number of repetition of the rotation of the movable mirror 220 are preset in accordance with the arrangement of the camera 210 and the movable mirror 220 and stored in the storage device 103.

The iris image acquisition unit 2004 acquires an iris image from a group of images acquired by the capture unit 2003. Acquisition of an iris image from a group of images is performed by either the division image scheme or the composite image scheme described above.

The iris recognition unit 2005 recognizes whether or not the user A is allowed to pass the gate 250 by using a known iris recognition method based on the iris image acquired by the iris image acquisition unit 2004. Specifically, the iris recognition unit 2005 extracts the pattern of the iris from the iris image acquired by the iris image acquisition unit 2004 and extracts information similar to the pattern as information on the user A in accordance with a predetermined criterion. The iris recognition unit 2005 then allows passage of the gate 250 if the information on the user A indicates authority of passage of the gate 250 and, otherwise, rejects passage of the gate 250.

The gate control unit 2006 transmits an electrical signal to the gate 250 to open or close the gate 250 based on the determination performed by the iris recognition unit 2005.

Figure 14:
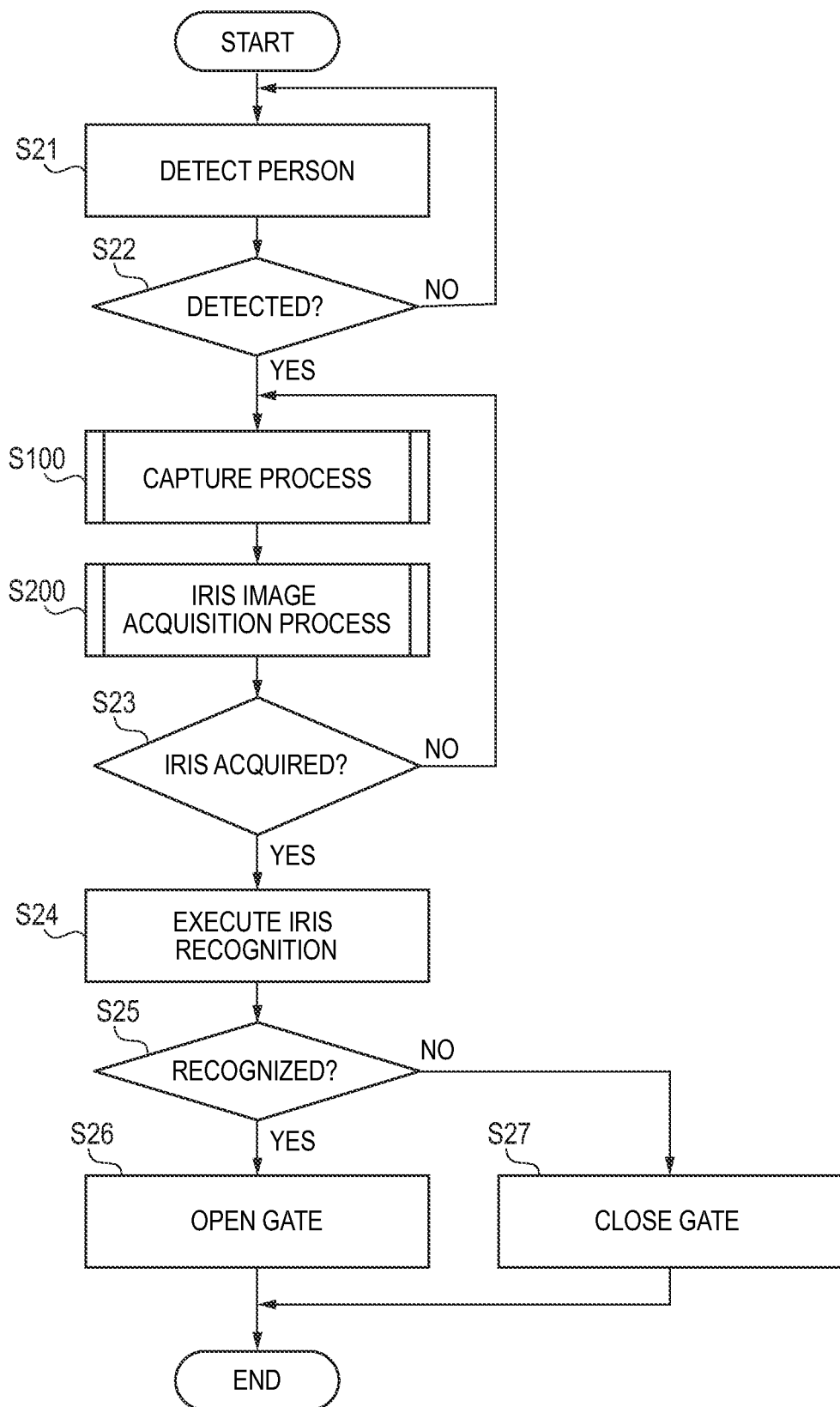
FIG. 14 is a diagram illustrating a flowchart of an iris image capture method according to the second example embodiment.

FIG. 14 is a diagram illustrating a flowchart of an iris capture method according to the present example embodiment. First, the human detection unit 2001 uses the human sensor 240 to detect whether or not the user A is present within the detecting range (step S21). If the user A is not detected in step S21 (step S22, NO), step S21 is repeated every predetermined time. If the user A is detected (step S22, YES), the iris capture apparatus 200 acquires an image of the face of the user A within the scan region J using a capture process illustrated in FIG. 8 (step S100). Next, the iris capture apparatus 200 acquires an iris image of the user A using the iris image acquisition process illustrated in FIG. 9 and FIG. 10 from the image of the face of the user A acquired in step S100 (step S200). If no iris image is acquired in step S200 (step S23, NO), the capture apparatus of step S100 and the iris image acquisition process of step S200 are repeated within the scan region J.

If an iris image is acquired in step S200 (step S23, YES), the iris recognition unit 2005 recognizes whether or not the user A is allowed to pass through the gate 250 using a known iris recognition method based on an iris image acquired by the iris image acquisition unit 2004 (step S24). If the user A is recognized in step S24 (step S25, YES), the gate control unit 2006 opens the gate 250 (step S26). If the user A is not recognized in step S24 (step S25, NO), the gate control unit 2006 closes the gate 250 (step S27).

The present invention captures a user by rotating a mirror and therefore can quickly acquire a high resolution iris image. Thus, by repeatedly attempting acquisition of an iris image in a space on a path on which the user moves as described in the present example embodiment, even when the user is moving, the iris image thereof can be acquired and walk-through recognition can be realized.

Other Example Embodiments

Figure 15:
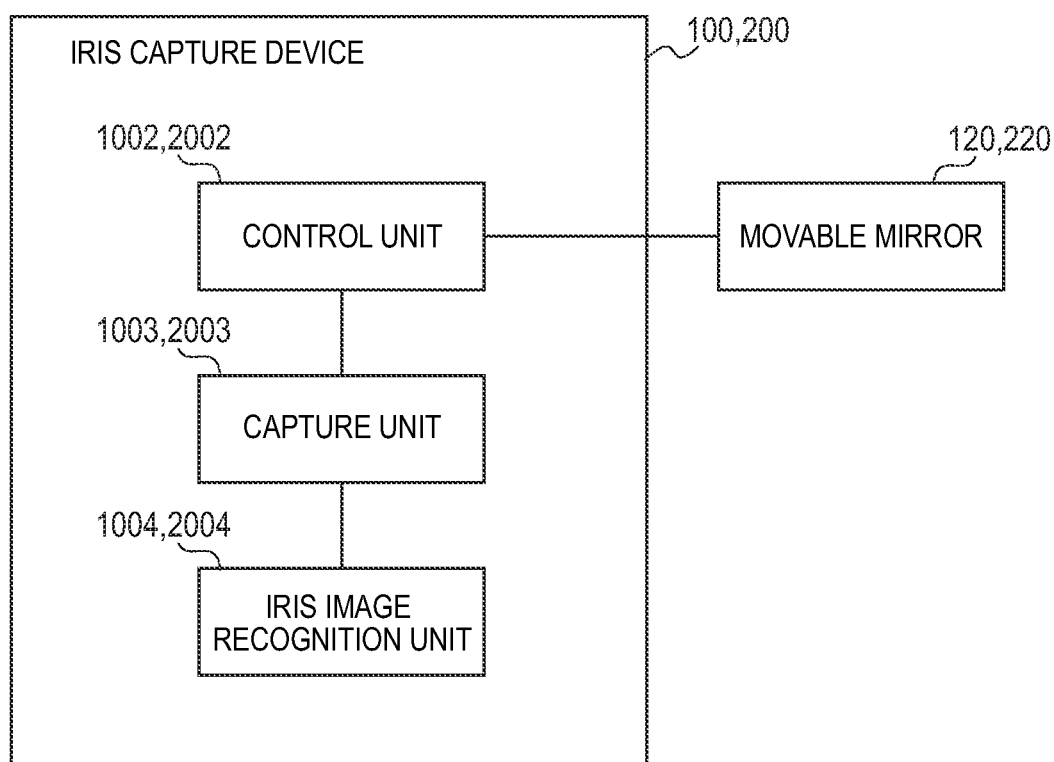
FIG. 15 is a schematic configuration diagram of the iris capture apparatus according to each example embodiment.

FIG. 15 is a schematic configuration diagram of the iris capture apparatuses 100 and 200 according to respective example embodiments described above. FIG. 15 illustrates a configuration example for implementing the function of the iris capture apparatuses 100 and 200 acquiring an image of a user's iris. The iris capture apparatuses 100 and 200 have the rotatable movable mirrors 120 and 220, the control units 1002 and 2002 that control rotation of the movable mirrors 120 and 220, the capture units 1003 and 2003 that capture different regions of a face of a user via the movable mirrors 120 and 220 and output a group of images every time the control units 1002 and 2002 rotate the movable mirrors 120 and 220 by a predetermined angle, and the iris image acquisition units 1004 and 2004 that acquire an image of an iris of the user from the group of images, respectively.

The present invention is not limited to the example embodiments described above and can be changed as appropriate within a range not departing from the spirits of the present invention.

A processing method that stores a program that operates the configuration of the example embodiment to implement the function of each example embodiment described above (more specifically, the program that causes a computer to execute the method illustrated in FIG. 7 to FIG. 10 and FIG. 14) in a storage medium, reads the program stored in the storage medium as a code, and executes it in a computer is also included in the scope of each example embodiment. That is, a computer readable storage medium is also included in the scope of each example embodiment. Further, not only the storage medium in which the program described above is stored but also the program itself is included in each example embodiment.

As the storage medium, for example, a floppy (registered trademark) disk, a hard disk, an optical disk, a magneto-optical disk, a CD-ROM, a magnetic tape, a non-volatile memory card, or a ROM may be used. Further, without being limited to one executing the process with only the program stored in the storage medium, those operating on an OS to execute the process in corporation with other software or the function of an extension board is included in the scope of each example embodiment.

The whole or part of the example embodiments disclosed above can be described as, but not limited to, the following supplementary notes.

(Supplementary Note 1)

An iris capture apparatus comprising:

a rotatable movable mirror;

a control unit that controls rotation of the movable mirror;

a capture unit that captures different regions of a face of a user via the movable mirror and outputs a group of images every time the control unit rotates the movable mirror by a predetermined angle; and an iris image acquisition unit that acquires an image of an iris of the user from the group of images.

(Supplementary Note 2)

The iris capture apparatus according to supplementary note 1, wherein respective parts of two neighboring regions of the regions overlap with each other.

(Supplementary Note 3)

The iris capture apparatus according to supplementary note 1 or 2, wherein the iris image acquisition unit determines a position of the iris of the user by calculating a feature amount from the group of images and comparing the feature amount with a feature amount of a pre-stored iris.

(Supplementary Note 4)

The iris capture apparatus according to supplementary note 1 or 2, wherein the iris image acquisition unit determines a position of the iris of the user by composing the group of images to generate a composite image and detecting a position of an eye included in the composite image.

(Supplementary Note 5)

The iris capture apparatus according to any one of supplementary notes 1 to 4, wherein the movable mirror is rotatable about a first axis, and wherein, by the control unit rotating the movable mirror about the first axis for a predetermined number of times, the capture unit captures the entire region of the face of the user.

(Supplementary Note 6)

The iris capture apparatus according to any one of supplementary notes 1 to 4, wherein the movable mirror is rotatable about a first axis and a second axis, and wherein, by the control unit rotating the movable mirror about the first axis and the second axis for a predetermined number of times, the capture unit captures the entire region of the face of the user.

(Supplementary Note 7)

The iris capture apparatus according to any one of supplementary notes 1 to 6 further comprising an iris recognition unit that recognizes the user based on the image of the iris.

(Supplementary Note 8)

The iris capture apparatus according to supplementary note 7 further comprising a gate that can be opened and closed, wherein the iris recognition unit recognizes whether or not the user is allowed to pass through the gate based on the image of the iris.

(Supplementary note 9)

The iris capture apparatus according to supplementary note 8, wherein the capture unit repeatedly captures a space over a path on which the user moves to the gate until the iris image acquisition unit successfully acquires the image of the iris.

(Supplementary Note 10)

The iris capture apparatus according to any one of supplementary notes 1 to 9 further comprising a light source that irradiates the user with a light, wherein the light source is arranged such that the region is irradiated with the light via the movable mirror.

(Supplementary Note 11)

The iris capture apparatus according to any one of supplementary notes 1 to 10, wherein the movable mirror has a stepping motor, and the control unit rotates the movable mirror by driving the stepping motor.

(Supplementary Note 12)

An iris capture method comprising steps of:

rotating a rotatable movable mirror repeatedly by a predetermined angle;

capturing different regions of a face of a user via the movable mirror and outputting a group of images every time rotating the movable mirror by a predetermined angle; and acquiring an image of an iris of the user from the group of images.

(Supplementary Note 13)

A storage medium that causes a computer to execute steps of rotating a rotatable movable mirror repeatedly by a predetermined angle;

capturing different regions of a face of a user via the movable mirror and outputting a group of images every time rotating the movable mirror by a predetermined angle; and acquiring an image of an iris of the user from the group of images.

The invention claimed is:

1. An iris capture apparatus comprising:
a processor configured to:
activate a human sensor;
acquire, after the human sensor has detected a user, a first image, the first image depicting an iris of the user, by rotating a rotatable movable mirror, using a motor, of the iris capture apparatus in a first direction;
determine whether the iris is depicted in the first image;
rotate the rotatable movable mirror again, using the motor, in response to the iris not being depicted in the first image, to acquire a second image; and
recognize the user based on an acquired image of the iris,
wherein the processor is configured to capture a third image, the third image depicting iris of the user, from the second image,
wherein the rotatable movable mirror of the iris capture apparatus is rotatable about a first axis, and wherein the processor is configured to rotate the rotatable movable mirror of the iris capture apparatus about the first axis for a predetermined number of times, and
wherein respective parts of two neighboring capturing regions of the iris capture apparatus overlap with each other in a predetermined direction.

2. The iris capture apparatus according to claim 1, wherein the third image has a higher resolution than the second image.

3. The iris capture apparatus according to claim 1, wherein the processor is configured to determine a position of the iris of the user by calculating a feature amount from the group of images and comparing the feature amount with a feature amount of a pre-stored iris.

4. The iris capture apparatus according to claim 1, wherein the processor is configured to determine a position of the iris of the user by composing the group of images to generate a composite image and detecting a position of an eye included in the composite image.

5. The iris capture apparatus according to claim 1, further comprising a gate that can be opened and closed, wherein the processor is configured to recognize whether or not the user is allowed to pass through the gate based on the image of the iris.

6. The iris capture apparatus according to claim 5, wherein the processor is configured to repeatedly capture a space over a path on which the user moves to the gate until the iris image acquisition unit successfully acquires the image of the iris.

7. The iris capture apparatus according to claim 1, further comprising a light source that irradiates the user with a light, wherein the light source is arranged such that the region is irradiated with the rotatable movable mirror of the iris capture apparatus.

8. The iris capture apparatus according to claim 1, wherein, after acquiring the second image, the processor is configured to capture a third image, the third image depicting iris of the user.

9. A method of iris capturing comprising:
activating a human sensor;
acquiring a first image after the human sensor has detected a user, the first image depicting an iris of the user, by rotating a rotatable movable mirror, using a motor, of the iris capture apparatus in a first direction;
determining whether the iris is depicted in the first image;
rotating the rotatable movable mirror again, using the motor, in response to the iris not being depicted in the first image, to acquire a second image; and
recognizing the user based on an acquired image of the iris,
wherein the method further comprises capturing a third image, the third image depicting iris of the user, from the second image,
wherein the rotatable movable mirror of the iris capture apparatus is rotatable about a first axis, and wherein the method further comprises rotating the rotatable movable mirror of the iris capture apparatus about the first axis for a predetermined number of times, and
wherein respective parts of two neighboring capturing regions of the iris capture apparatus overlap with each other in a predetermined direction.

10. A non-transitory computer readable medium having stored therein a program for performing a method of iris capturing comprising:
activating a human sensor;
acquiring a first image after the human sensor has detected a user, the first image depicting an iris of the user, by rotating a rotatable movable mirror, using a motor, of the iris capture apparatus in a first direction;
determining whether the iris is depicted in the first image;
rotating the rotatable movable mirror again, using the motor, in response to the iris not being depicted in the first image, to acquire a second image; and
recognizing the user based on an acquired image of the iris, wherein the method further comprises capturing a third image, the third image depicting iris of the user, from the second image, wherein the rotatable movable mirror of the iris capture apparatus is rotatable about a first axis, and wherein the method further comprises rotating the rotatable movable mirror of the iris capture apparatus about the first axis for a predetermined number of times, and wherein respective parts of two neighboring capturing regions of the iris capture apparatus overlap with each other in a predetermined direction.

\* \* \* \* \*